(12) United States Patent
Schmid et al.

(10) Patent No.: US 9,295,767 B2
(45) Date of Patent: Mar. 29, 2016

(54) HEART ASSISTANCE DEVICE

(75) Inventors: Thomas Schmid, Herrsching (DE);
Bernhard Vodermayer, Germering (DE); Heinrich Gmeiner, Waldthurn (DE); Alexandra Wimmer, Munich (DE); Andreas Kunz, Erbendorf (DE); Wolfgang Schiller, Bonn (DE)

(73) Assignee: DEUTSCHES ZENTRUM FUER LUFT-UND RAUMFAHRT E.V., Cologne (DE)

( * ) Notice: Subject to any disclaimer, the term of this patent is extended or adjusted under 35 U.S.C. 154(b) by 323 days.

(21) Appl. No.: 13/642,783

(22) PCT Filed: Apr. 21, 2011

(86) PCT No.: PCT/EP2011/056448
§ 371 (c)(1),
(2), (4) Date: Jan. 31, 2013

(87) PCT Pub. No.: WO2011/131766
PCT Pub. Date: Oct. 27, 2011

(65) Prior Publication Data
US 2013/0218268 A1    Aug. 22, 2013

(30) Foreign Application Priority Data

Apr. 23, 2010   (DE) .......................... 10 2010 018 233

(51) Int. Cl.
*A61M 1/10* (2006.01)
*A61M 1/12* (2006.01)

(52) U.S. Cl.
CPC ............... *A61M 1/101* (2013.01); *A61M 1/106* (2013.01); *A61M 1/1029* (2014.02);
(Continued)

(58) Field of Classification Search
CPC ..... A61M 1/10; A61M 1/1005; A61M 1/101; A61M 1/1029; A61M 1/1032; A61M 1/1037; A61M 1/1044; A61M 1/106
USPC ....................................... 623/3.1–3.3
See application file for complete search history.

(56) References Cited

U.S. PATENT DOCUMENTS

| | | | |
|---|---|---|---|
| 4,255,821 A | | 3/1981 | Carol |
| 4,376,312 A | * | 3/1983 | Robinson et al. ............. 623/3.21 |
| 4,704,120 A | | 11/1987 | Slonina |
| 4,750,903 A | * | 6/1988 | Cheng ........................... 623/3.25 |

(Continued)

FOREIGN PATENT DOCUMENTS

| | | |
|---|---|---|
| DE | 2730933 | 1/1979 |
| DE | 10062153 | 12/2000 |

(Continued)

OTHER PUBLICATIONS

International Search Report dated Jul. 27, 2011 for PCT application No. PCT/EP2011/056448.

(Continued)

*Primary Examiner* — David Isabella
*Assistant Examiner* — Suba Ganesan
(74) *Attorney, Agent, or Firm* — Ohlandt, Greeley, Ruggiero & Perle, L.L.P.

(57) ABSTRACT

A heart assistance device for the pulsatile delivery of blood is provided that includes a first pump chamber, a second pump chamber, and a pump. Both pump chambers each have a fluid chamber and a blood-carrying chamber. By means of the pump, each fluid chamber can be filled with a fluid or emptied thereof in such a way that an expansion or contraction of the fluid chamber takes place. During the expansion of the fluid chamber of one pump chamber, a compression of the blood-carrying chamber of the same blood chamber takes place. The pump is designed as a roller cell pump or vane pump.

3 Claims, 4 Drawing Sheets

(52) U.S. Cl.
CPC .......... *A61M 1/1037* (2013.01); *A61M 1/1063* (2014.02); *A61M 1/1065* (2014.02); *A61M 1/122* (2014.02); *A61M 1/107* (2013.01)

(56) References Cited

U.S. PATENT DOCUMENTS

| | | |
|---|---|---|
| 2007/0073303 A1 | 3/2007 | Namba |
| 2011/0137107 A1 | 6/2011 | Vodermayer et al. |

FOREIGN PATENT DOCUMENTS

| | | |
|---|---|---|
| DE | 102008017448 A1 | 10/2009 |
| EP | 2078533 | 7/2009 |
| FR | 1460721 A | 3/1966 |
| FR | 2585249 | 1/1987 |
| FR | 2710847 | 4/1995 |
| GB | 1307135 | 2/1973 |
| GB | 2332481 | 6/1999 |
| RU | 2131271 | 6/1999 |
| WO | 9842894 | 10/1998 |
| WO | 9842984 A1 | 10/1998 |

OTHER PUBLICATIONS

Written Opinion dated Jul. 27, 2011 for PCT application No. PCT/EP2011/056448.

* cited by examiner

HEART ASSISTANCE DEVICE

BACKGROUND

1. Field of the Invention

The disclosure refers to a heart assistance device for the pulsatile delivery of blood.

2. Discussion of the Background Art

Mechanical circulatory support systems (VAD: ventricular assist devices) find clinical application for about 15 years and are the last option for the preservation of life in cases of manifested cardiac insufficiency. Heart assistance systems take over a part of the pumping work and thereby stabilize circulation until a donor organ is available. Recent studies have shown that, under this therapy, the heart function can improve as far as to allow an explantation of the system without subsequent heart transplantation.

Artificial heart pumps can be adapted to various requirements and are available without any waiting period. However, there are limitations with respect to the technology used and the compatibility. For example, the blood can be damaged by the pumping. The power supply to the systems, which are presently exclusively electrically operated, via wires through the abdominal wall, bears a high risk of infection for the patient.

Low degrees of efficiency lead to high energy consumption and to a heating up of the surrounding tissue. Assisted circulation often has to be kept up for months or years. Further, the systems are subjected to high mechanic stresses. Since a short-term replacement of the blood pumps is not possible, they have to feature a high durability and operational reliability.

With known drives for heart assistance devices the structural size makes implantability impossible to achieve in some cases. Further, a high wear of mechanical parts of the drive, and thus a shortening of the useful life, exist. Moreover, loud driving noises can occur. Other known disadvantages are a low degree of efficiency or a low output that translates as a low volume flow and an insufficient assistance. Known implantable pumps only have one pump chamber which can assist only one ventricle, preferably the left one. Further, implantable single chamber pumps additionally require a compensation for the volume delivered. Presently, this problem is solved with a volume compensation container (vent) that has to be implanted along with the device and causes additional complications.

It is an object of the present disclosure to provide an improved heart assistance device that in particular is simpler to implant.

SUMMARY

A heart assistance device for the pulsatile delivery of blood comprises a first and a second pump chamber as well as a pump. Each of the two pump chambers comprises a fluid chamber and a blood-carrying chamber, each fluid chamber being adapted to be filled with a fluid or emptied by means of the pump such that the fluid chamber is expanded or contracted. When the fluid chamber of a pump chamber is expanded, the blood-carrying chamber of the same pump chamber is compressed. According to the disclosure, the pump is designed as a roller cell pump or a vane pump.

In a preferred embodiment of the disclosure the pump operates in a reversing mode. This has the advantage that the necessary energy for the systemic circulation has to be made available only at the relevant times. Comparable hydraulic drives are known from prior art, which, however, use different pumping principles and therefore comprise more and larger moving parts. The result thereof is a higher moment of inertia and a lower degree of efficiency. Another advantage obtained from the use of a roller cell pump or a vane pump in an alternating mode is that fewer pressure surges occur and unnecessary friction losses are avoided. At the moment of a reversal of rotation the blocking bodies no longer have a sealing effect so that a pressure compensation can occur that is energetically favorable.

Generally, the drive of the disclosure comprises few moving parts, and thus comprises few friction components. The use of a suitable hydraulic liquid allows for a further reduction of the friction losses.

The above-mentioned avoidance of pressure surges results in reduced stress on all components connected with the hydraulic circuit. Therefore, fewer stress peaks are generated in the relevant components, such as the membranes, for example, whereby less wear is caused. It is another advantage that the roller cell pump or the vane pump has as a characteristic, depending on the configuration, not to build up further pressure once a specific pressure is achieved, whereby inherent safety is guaranteed. Thus, the pump has a mechanical pressure limitation that, in the extreme case, prevents the destruction of the implant.

It is advantageous to integrate the drive system formed by the alternating pump and the motor into the implant. Due to the high overall efficiency, the pump unit can be designed smaller as compared to other drive systems and therefore requires less volume in a patient's body.

The heart assistance device of the disclosure is therefore more compact, less prone to wear and more silent than known drive concepts, and, moreover, it can be operated for a longer period of time. Accordingly, a fully implantable system can be provided that minimizes the risk of infection for a patient. Further, a particularly high level of running smoothness can be achieved. The heart assistance device of the disclosure may be operated, for example, with double-chamber systems, such as the DLR-LVAS, or with systems having one pressure chamber and one compensation container.

In an alternative embodiment it is possible to operate the pump in one direction, the heart assistance device comprising valves to redirect the fluid flow.

As an alternative thereto, the heart assistance function can comprise two roller cell or vane pumps, each connected with a fluid chamber and alternately delivering in opposed directions. Here, the quantity of fluid delivered into the fluid chambers is adjustable via the rotational speed of the roller cell or vane pump.

Depending on the arrangement, it may be advantageous to additionally connect an external compensation chamber to the hydraulic system of the pump. Thereby, an additional safety factor is provided, since pressure surges that the hydraulic pump does not absorb and that can damage the structure of the system have to be attenuated. Here, the connection can be made near the hydraulic pump or at the respective hydraulic chambers.

It is particularly preferred that the heart assistance device comprises a housing, the two pump chambers and the pump itself being arranged in the housing and the pump being arranged between the pump chambers. This allows for a particularly flat structure. The pump chamber can comprise a flexible blood chamber and a fluid chamber with a rigid or flexible housing.

As an alternative, the two pump chambers can be arranged inside the housing, while the pump is arranged outside the housing and is connected with the pump chambers via rigid or flexible lines. Thereby, a flexible arrangement can be achieved.

In a further alternative embodiment each pump chamber has its own housing, wherein these housings are not interconnected and the pump chambers are connected with each other in particular exclusively via the pump and rigid or flexible lines between the pump and the pump chambers. Thus, the drive forms a flexible connection between the components.

In another alternative embodiment each pump chamber has its own housing, both housings being connected through a joint. The same may be, for instance, a ball joint, a hinge or another suitable joint. Also in this case, the pump is arranged outside the housing and is connected with the pump chambers through rigid or flexible lines.

In another alternative embodiment the two pump chambers are not connected directly, but in particular exclusively through the pump and or rigid or flexible lines between the pump and the pump chambers. Here, both pump chambers are enclosed by a common flexible membrane, with the pump being arranged either inside or outside the membrane. This allows for a flexible arrangement of the pump chambers.

In all embodiments described above, the pump chambers can comprise a flexible blood chamber and a fluid chamber with a rigid or flexible housing.

It is particularly preferred that the pump chambers are of a seamless design and comprise a reinforcement in the form of a stiffening element arranged at one or a plurality of pump chamber locations that are subjected to high mechanical stresses. It is further preferred to realize the pump chambers in a manner optimized in terms of flow. Due to the measures mentioned, the risk of deposits is minimized. Further, enhanced compression can be achieved, whereby minimal shearing of the blood is guaranteed, since no kinks are formed as they are known from prior art systems. The blood chamber comprises a flexible membrane, with the stiffening being either flexible or rigid.

It is particularly preferred for the stiffening element to present flow guiding elements on the outside for guiding the fluid flow.

The disclosure further refers to a method for operating a heart assistance device comprising two roller cell or vane pumps, each connected with a fluid chamber and alternately delivering in opposed directions. In the event of a failure of one of the pumps, the remaining pump switches to a reversing operation mode and thus takes over the entire pumping effort. Thereby, an increased resilience can be achieved.

The disclosure further refers to the use of a roller cell pump or a vane pump as a drive for a heart assistance device with two blood chambers.

The following is a detailed description of preferred embodiment of the disclosure with reference to the Figures.

DETAILED DESCRIPTION OF THE PREFERRED EMBODIMENT

Figure 1:
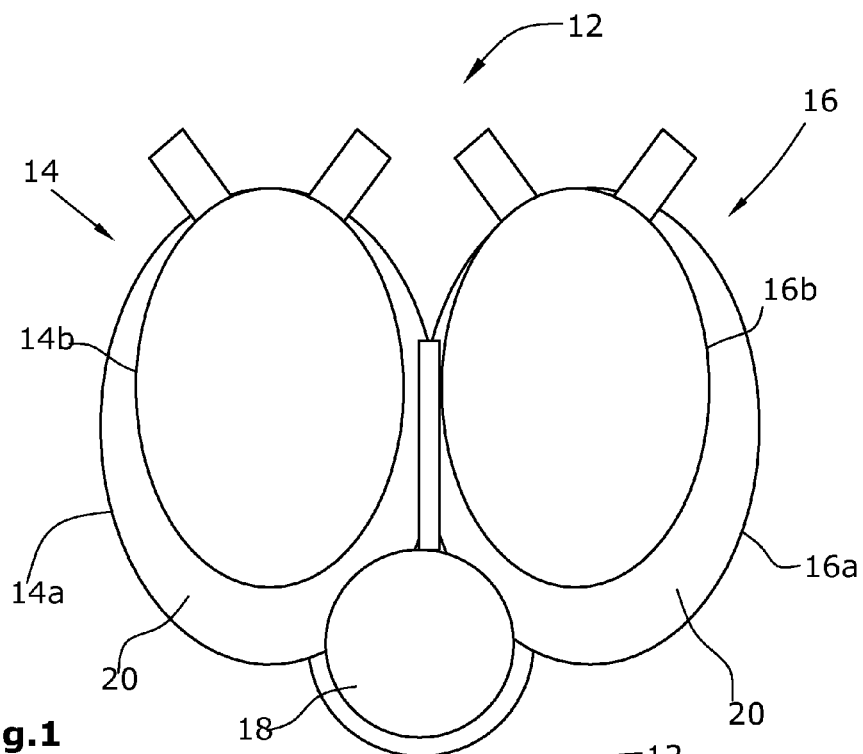
FIGS. 1-5 are schematic illustrations of different possible arrangements of the pump in the heart assistance device of the disclosure.

Referring to FIG. 1, the heart assistance device comprises a first 14 and a second pump chamber 16, as well as a pump 18. The pump has connections to the left and the right pump chamber and is arranged between the pump chambers. The entire device comprises a common housing. That means that both pump chambers 14, 16, as well as the pump 18 are arranged in this housing.

Figure 2:
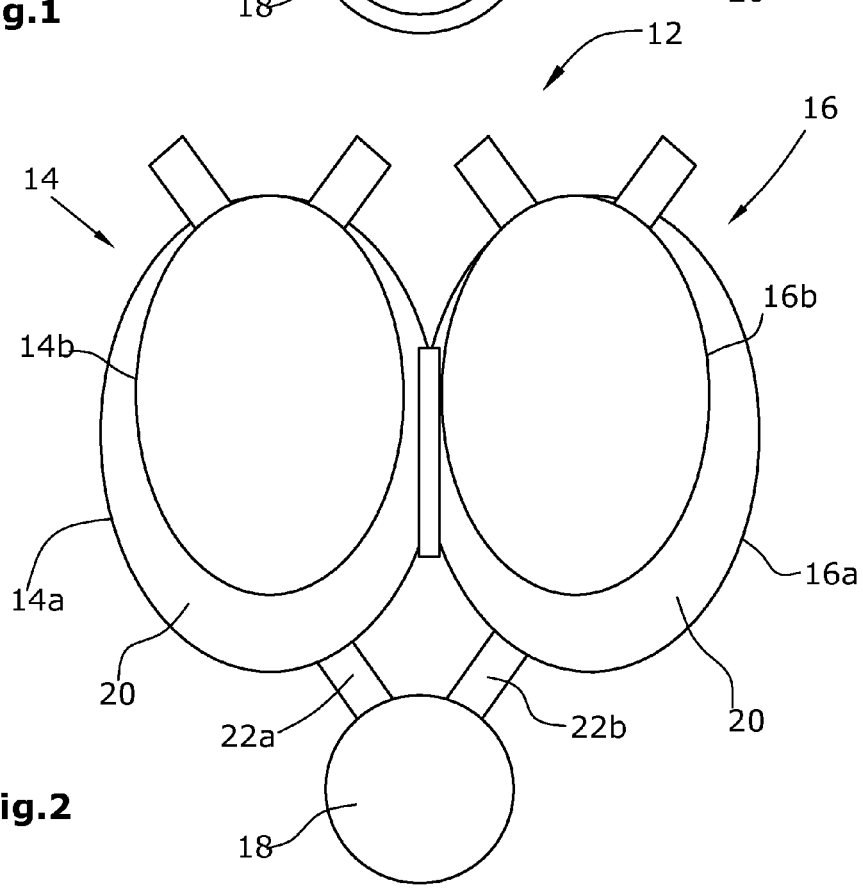

Referring to FIG. 2, it is possible as an alternative to arrange the two pump chambers 14, 16 in the housing and to arrange the pump 18 outside the housing and to connect the pump with the pump chambers 14, 16 via rigid or flexible lines 22a, 22b. Thus, the drive can be arranged between the pump chambers 14, 16 in a flexible manner.

Figure 3:
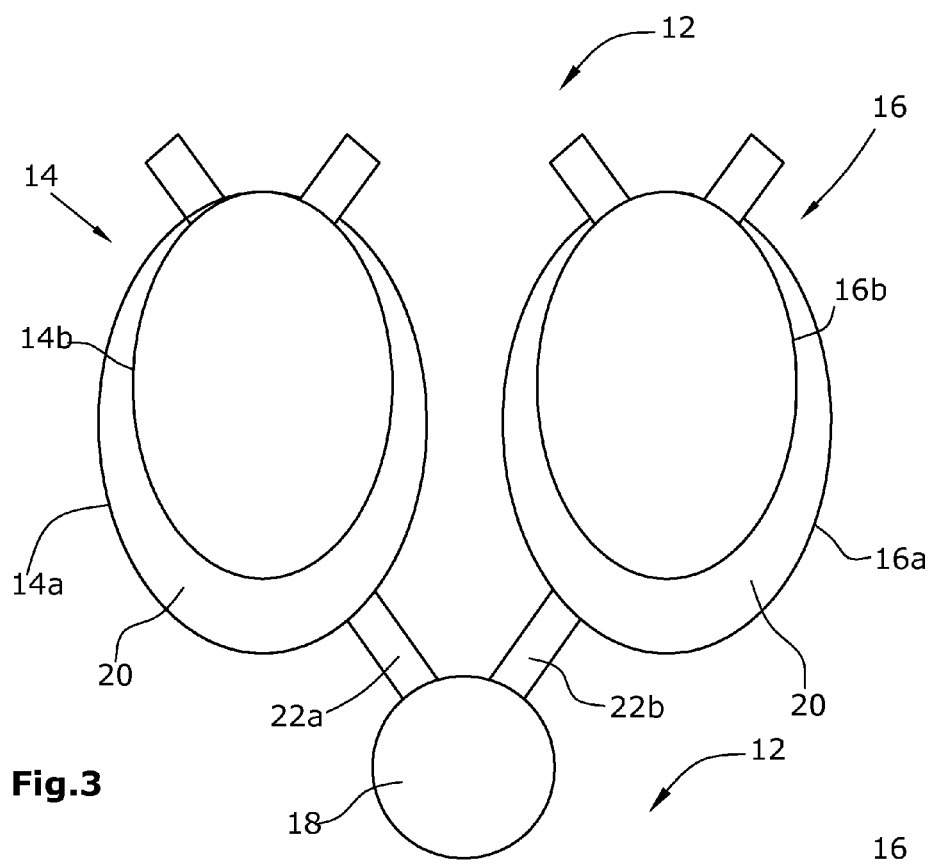

In the embodiment illustrated in FIG. 3 each pump chamber 14, 16 comprises a housing of its own, wherein these housings are not interconnected and the pump chambers 14, 16 are exclusively connected with each other via the pump 18 and rigid or flexible lines 22a, 22b between the pump 18 and the pump chambers 14, 16.

Figure 4:
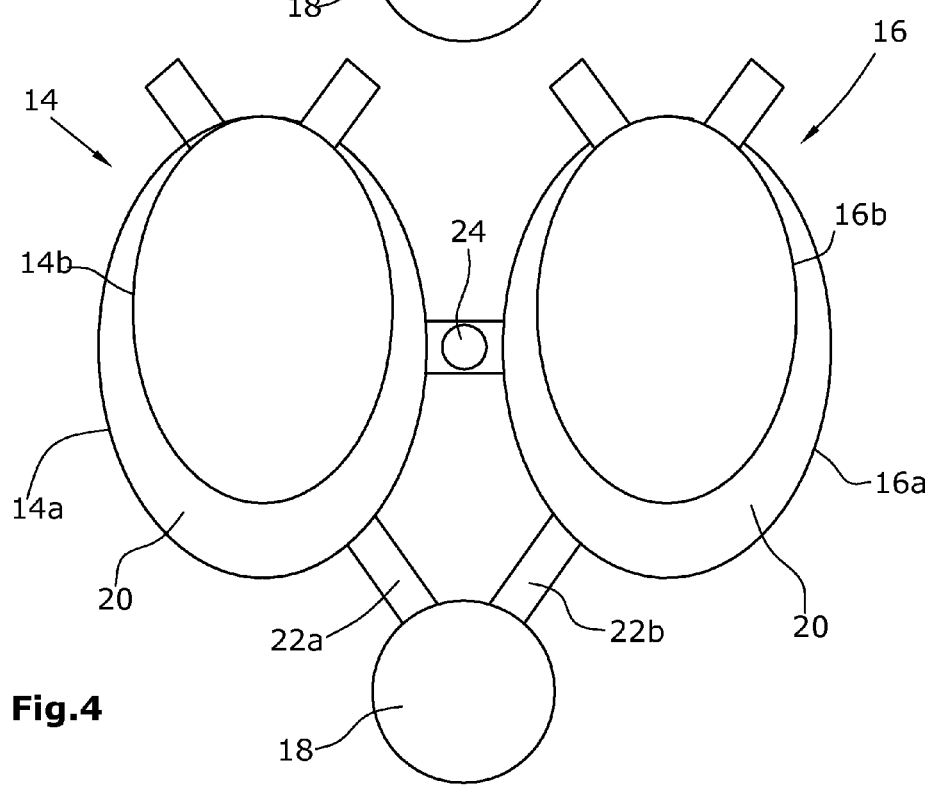

In the embodiment illustrated in FIG. 4 each pump chamber 14, 16 also has a housing of its own, with the housings being connected by means of a joint 24. Again the pump 18 is arranged outside the housing and is connected with the pump chambers 14, 16 via lines 22a, 22b.

Figure 5:
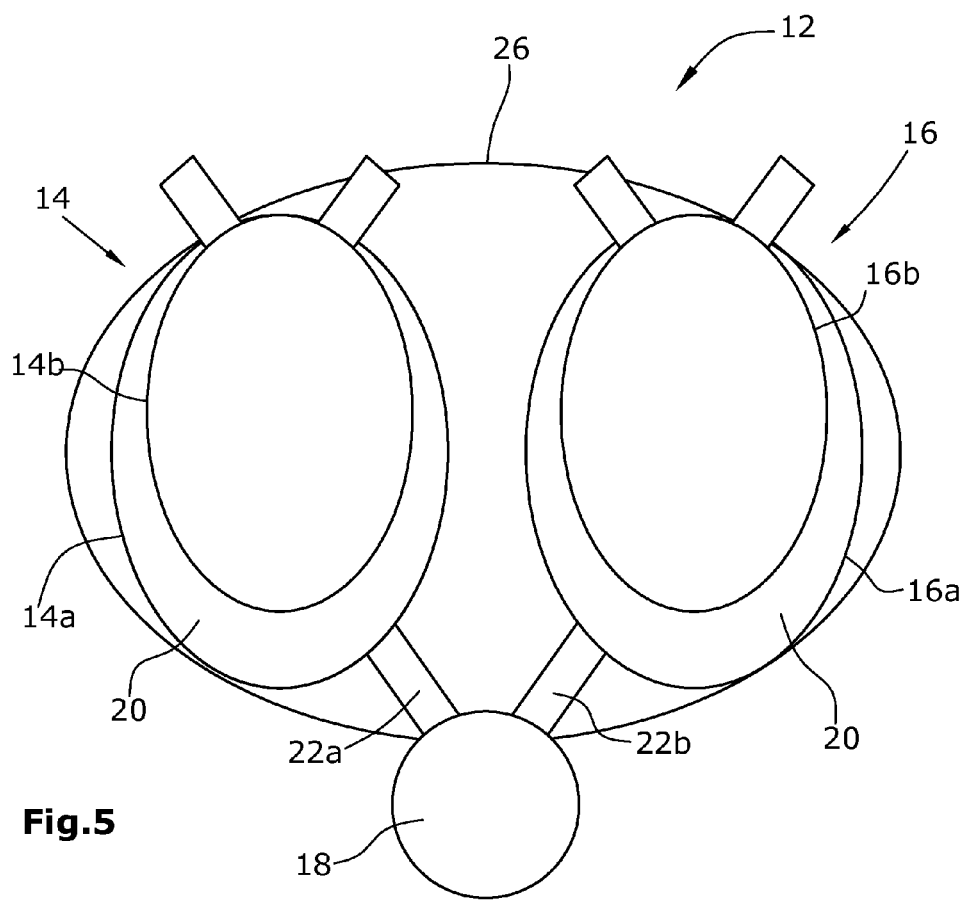

The embodiment illustrated in FIG. 5 comprises a common flexible membrane 26 surrounding the two pump chambers 14, 16. The pump 18 can be arranged inside or outside the membrane 26. The pump 18 is connected with the pump chambers 14, 16 by means of flexible or rigid lines 22a, 22b.

Figure 6:
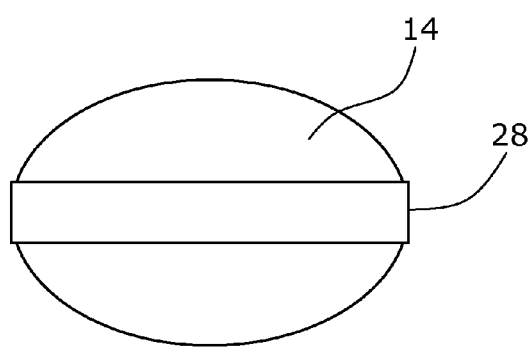
FIG. 6 is a schematic illustration of a blood chamber with an integrated stiffening element.

FIG. 6 shows a schematic illustration of a seamless, flow-optimized pump chamber comprising a stiffening element 28 at the location most subjected to stress. This stiffening element 28 may have flow guiding elements, not illustrated, on its outer side for guiding the fluid flow.

FIGS. 1-5 illustrate a bi-ventricular heart assistance system comprising two main chambers or blood chambers 14, 16 that are preferably formed from a pressure-resistant material. For the left half of the heart, supply and discharge lines for the transportation of blood are connected to the left ventricle (inlet of the pump) and to the aorta (outlet of the pump). In analogy with the left half of the heart, the connections for the right half of the heart are made to the right ventricle and the pulmonary artery. In heart assistance, the natural heart remains in the body, while the assistance system assumes a part of the pumping work and thereby relieves the natural heart.

A membrane or a flexible pumping bag divides each blood chambers 14, 16 into a blood-carrying chamber 14b, 16b and a fluid or hydraulic chamber 14a, 16a. When pressure is built up in this fluid chamber, the pressurized blood chamber is simultaneously compressed. The blood volume is reduced in favor of the hydraulic volume and the volume in the blood chamber is emptied into circulation after the flaps at the outlet have been opened. The flaps are each arranged at a supply and a discharge at the blood-carrying chambers such that a unidirectional blood flow is guaranteed.

By the above described arrangement of the chambers 14, 16 and the hydraulic pump 18 it is possible to fill one blood chamber as the other blood chamber is compressed. Due to the incompressibility of the hydraulic fluid, the second blood chamber can also be filled by suction, whereby a constant blood deliver rate is guaranteed. When the first blood chamber 14b is emptied, the direction of rotation of the hydraulic pump 18 is reversed and the second blood chamber 16b, now filled, is emptied, while the first blood-carrying chamber 14b is refilled.

Figure 7:
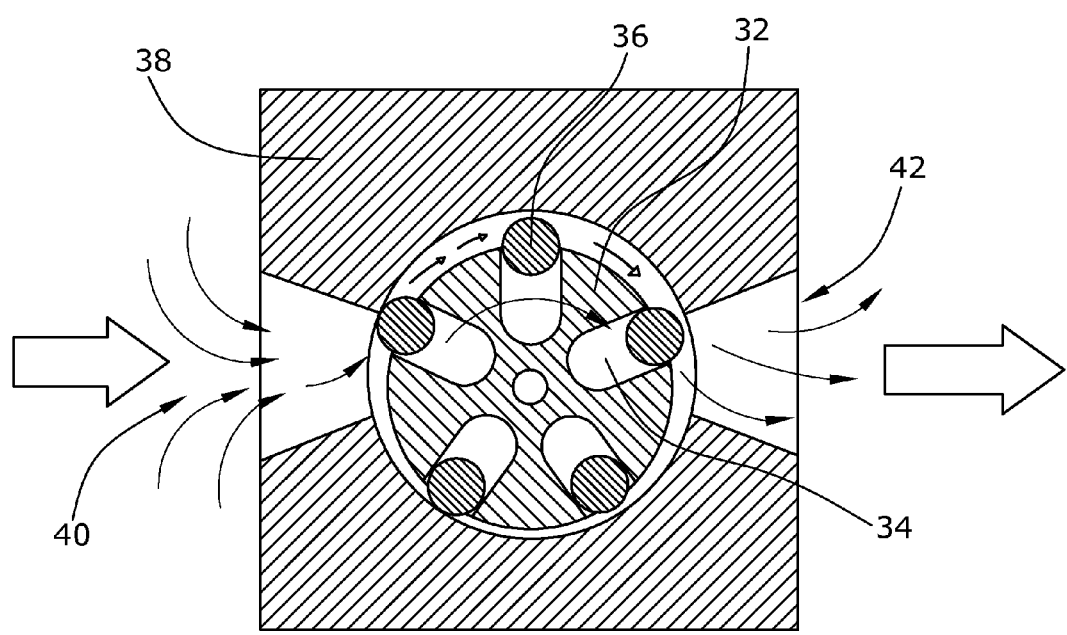
FIG. 7 is a schematic illustration of a roller cell pump.

A roller cell pump as illustrated in FIG. 7 may be used to convey the fluid. This pump comprises a cylindrical rotor 32 comprising a number of radial milled slots or recesses 34 arranged at regular intervals along its circumference. The depth and the shape of the milled slots 34 are chosen such that a cylindrical blocking body 36, whose diameter is at most equal to the width of the milled slot 34, can sink completely into this milled slot 34 such that the round surface of the blocking body 36 is flush with the circumference of the rotor 32. Preferably, the blocking bodies 36 are roller cylinders. All milled slots 34 are respectively provided with a blocking body 36.

The rotor 32 is housed in a round pump chamber 38 (stator), with the stator 38 and the rotor 32 being arranged eccentrically. The stator 38 has two lateral openings 40, 42 that serve as an inlet or outlet opening for the hydraulic fluid, depending on the direction of rotation of the rotor 32.

The blocking bodies 36 are movable within the limits of the eccentricity determined by the rotor position and are pressed against the wall of the stator 38 by centrifugal forces. The eccentricity and the positions of the inlet and outlet openings 40, 42 are designed such that two adjacent blocking bodies 36 sealingly block a partial volume in the area of maximum eccentricity between the inlet and outlet openings. Due to the rotation of the rotor arrangement, a volume is thus displaced from the inlet opening to the outlet opening.

The roller cell pump may be designed such that the direction of the volume flow can be reversed by changing the direction of rotation. The axis of the rotor 32 simultaneously forms the shaft of a non-illustrated compact electric motor providing for the rotational movement of the rotor 32.

Preferably, the hydraulic fluid used is a liquid other than the blood of a patient, which liquid is biocompatible or even hemocompatible. Biocompatibility can be achieved with various silicone oils. If, for example, a saline solution is used, it is even possible to achieve hemocompatibility.

Due to the fact that the entire pump unit is situated in the hydraulic fluid and is constantly washed in the same, good heat dissipation from the electric motor can be achieved. Further, the heat buffered in the hydraulic fluid can be transferred to the blood in the pump chambers 14, 16. Since this process is continuous, there is no risk of heat being trapped, whereby the risk for the patient can be reduced. The service life of the pump is extended because of the uniform temperature prevailing.

As mentioned above, the arrangement can be driven by a single drive that constantly reverses its direction of rotation. As an alternative, a second hydraulic pump can be used, whereby a dedicated hydraulic pump is provided for each pumping direction. A reversal of directions that is detrimental to the drive shaft is excluded in this case, since each hydraulic pump only changes the rotational speed, but not the direction of rotation.

Preferably, the roller cell rotor (pump rotor) is arranged between two bearings 44, 46, where an electric drive is used that preferably is configured as a brushless electric motor.

As an alternative to the roller cell technology, a vane pump could also be used as the pump, wherein the blocking bodies are designed as flat plates instead of cylindrical rollers. The basic function of the pump remains unchanged.

What is claimed is:

1. A method for operating a heart assistance device, wherein the device comprises a first and a second pump chamber, and a pump, each of the pump chambers comprising a fluid chamber and a blood-carrying chamber, and each fluid chamber being adapted to be filled with or emptied of a fluid by means of the pump such that an expansion or contraction of the fluid chamber occurs, the blood-carrying chamber of the same pump chamber is compressed upon the expansion of the fluid chamber of said respective pump chamber, wherein the pump is a roller cell pump or a vane pump, and wherein the heart assistance device comprises two roller cell or vane pumps, each being connected with said respective fluid chamber and alternately delivering in opposed directions, the quantity of fluid delivered into the fluid chambers being adjustable through the rotational speed of the first or the second roller cell or vane pump, the method comprising:
   wherein in the event of a failure of one of the two pumps, the remaining pump switches to a reversing mode and takes over all of the pumping work.

2. A method for operating a heart assistance device, comprising:
   providing a first pump chamber having a first fluid chamber and a first blood-carrying chamber;
   providing a second pump chamber having a second fluid chamber and a second blood-carrying chamber;
   providing a first pump in fluid communication with the first and second fluid chambers;
   providing a second pump fluid communication with the first and second fluid chambers;
   operating the first pump in only a first pumping direction to pump hydraulic fluid from the first fluid chamber to the second fluid chamber to cause the first fluid chamber to contract and the second fluid chamber to expand, resulting in expansion of the first blood-carrying chamber and contraction of the second blood-carrying chamber;
   operating the second pump in only a second pumping direction to pump hydraulic fluid from the second fluid chamber to the first fluid chamber to cause the second fluid chamber to contract and the first fluid chamber to expand, resulting in expansion of the second blood-carrying chamber and contraction of the first blood-carrying chamber; and
   switching a remaining operational pump of the first and second pumps, in the event of a failure of the other of the first and second pumps, to a reversing mode in which the remaining operational pump pumps in both the first and second pumping directions to takes over all of the pumping work.

3. The method of claim 2, further comprising adjusting a rotational speed of the first and/or second pumps to adjust a quantity of the hydraulic fluid delivered between the first and second fluid chambers.

* * * * *